(12) United States Patent
Halverson et al.

(10) Patent No.: US 6,192,598 B1
(45) Date of Patent: Feb. 27, 2001

(54) MICROWAVE AND MILLIMETER WAVE METHOD AND APPARATUS FOR CONTROLLING INSECTS IN STORED-PRODUCTS

(75) Inventors: Steven L. Halverson, Clinton, WI (US); Timothy S. Bigelow, Knoxville, TN (US)

(73) Assignee: Micro-Grain, Inc., Clinton, WI (US)

( * ) Notice: Subject to any disclaimer, the term of this patent is extended or adjusted under 35 U.S.C. 154(b) by 0 days.

(21) Appl. No.: 09/459,275

(22) Filed: Dec. 13, 1999

Related U.S. Application Data

(62) Division of application No. 09/132,011, filed on Aug. 10, 1998.
(60) Provisional application No. 60/064,138, filed on Nov. 3, 1997.

(51) Int. Cl.[7] .................................................. F26B 17/12
(52) U.S. Cl. ................................................................ 34/174
(58) Field of Search ........................... 34/259, 265, 165, 34/168, 170, 174

(56) References Cited

U.S. PATENT DOCUMENTS

| | | | |
|---|---|---|---|
| 2,299,299 | * 10/1942 | Bills | 98/56 |
| 3,001,465 | * 9/1961 | Donelson, Jr. | 98/55 |
| 5,869,816 | * 2/1999 | Strack et al. | 219/687 |

* cited by examiner

*Primary Examiner*—Denise L. Ferensic
*Assistant Examiner*—Malik N. Drake
(74) *Attorney, Agent, or Firm*—Lathrop & Clark LLP

(57) ABSTRACT

A method and apparatus for disinfecting granular material using microwave energy in an applicator that mixes the material with air for consistent and effective insect mortality rates.

7 Claims, 4 Drawing Sheets

MICROWAVE AND MILLIMETER WAVE METHOD AND APPARATUS FOR CONTROLLING INSECTS IN STORED-PRODUCTS

This application is a divisional of Application No. 09/132,011 filed Aug. 10, 1998 and U.S. Provisional Application No. 60/064,138, filed Nov. 3, 1997, the disclosures of both applications are incorporated by reference herein

FIELD AND BACKGROUND OF THE INVENTION

This invention relates in general to pest control using microwave energy, and in particular to the use of Super High Frequency (SHF) and Extremely High Frequency (EHF) band microwaves that kill insects in granular materials without the use of chemicals.

The principle of using microwaves as a pesticide in grain and granular materials has been known, but it has been determined that effective and consistent mortality rates are only possible when the grain in unpacked, mixed with air, and fairly uniform in density for effective microwave penetration.

The search for an operating frequency which would lead to enhanced selective heating of insects in the Extremely High Frequency (EHF) and Super High Frequency (SHF) ranges is motivated by the need to develop alternatives to certain important agricultural chemical pesticides for the treatment of stored products which are to be banned by the Clean Air Act by the year 2001. Operation at discrete frequencies in the microwave and millimeter wave ranges, including Industrial Scientific and Medical (ISM) frequencies specified in the U.S. Code of Federal Regulations (47 C.F.R., part 2), is attractive because of the availability of recently developed high-power oscillators with high continuous outputs and efficiencies at those frequencies. Unlike the relatively low-power microwave and lower frequency heaters, operating at frequencies less than or equal to 2.45 GHz, the EHF and SHF high-power sources offer the possibility of continuous processing of the treated product at high throughput rates while taking advantage of the electromagnetic shielding inherent in the waveguide-like piping or duct systems that arc common in transport systems at grain storage facilities.

There is a need for a consistently effective microwave granular treatment device and microwave range that effects high mortality rates while maintaining temperatures within acceptable limits.

SUMMARY OF THE INVENTION

In accordance with the present invention there is a microwave device for controlling insect infestation in stored products such as bulk grains, granular or milled materials at typical processing and storage facilities, or packaging materials and containers used in the packaging of processed products. The device includes at least one high-power coherent nonionizing electromagnetic radiation means, emitting energy in the SHF (3 GHz to 30 GHz) or EHF (30 GHz to 300 GHz) band of the spectrum where coupling to the free water in the insect is maximized, power supplies to energize the radiation means, a cooling system for both the power source and the treated stored product that includes a heat exchanger for removal of waste heat and regenerative heating of the product, an electromagnetic energy transmission system, a process control system including sensors to monitor and control the process variables, active control elements to initiate and terminate product flow, a facility protection system to shut the system down when safe operating margins are exceeded, an applicator or interaction chamber through which the dynamic (flowing) product is uniformly mixed with atmospheric air by means of an applicator and to which the energy is coupled, a means of controlling the atmosphere within the applicator to avoid combustible mixtures of air and fine dust, and a treated product collector.

This invention uses energy in that portion of the SHF and EHF spectrum common with the relaxation processes associated with free water and hemolymph, uniquely associated with insects (Weber. 1974. Grundriss der Insektenkunde, Gustav Fischer Verlag, Stuttgart. pp 640 & Seifert. 1995. Entomologisches Praktikum, Georg Thieme Verlag Stuttgart-New York: 76–81.), to selectively heat and destroy the insects in stored products. Halverson et al. "Microwave Radiation As An Alternative To Chemical Pesticides", Paper No. 956129, ASAE Annual International Meeting, Chicago, Ill., Jul. 18–23, 1995; Halverson et al. "High-Power Microwave Radiation As An Alternative Insect Control Method For Stored-Products", J. Econ. Entomol. 89(6) 1638–1648 (1996); Halverson et al. "Effects Of SHF And EHF Radiation On The Mortality Of *S. zeamais* In Soft White Wheat", Paper No. 963013, ASAE Annual International Meeting, Phoenix, Ariz., Jul. 14–18, 1996; and in Plarre et al. 1997 disclosed testing of static infested samples of granular materials that maximum selective heating of insects occurs at exposers of discrete energy frequencies above 1 GHz.

Data taken with microwave network analyzers on samples of insects and white wheat and wheat flour, over frequency ranges from 50 MHz to 75 GHz, indicated that mortality of both *S. zeamais* and *Tribolium castaneum* (red flour beetle) is much greater at frequencies above about 24 GHz, confirming predictions obtained from analytical models (Halverson, et al. "SHF And EHF Microwave Radiation As A Pesticide Alternative For Stored Products", Paper No. 55, 1996 Annual International Research Conference on Methyl Bromide Alternatives and Emissions Reductions, Nov. 4–6, 1996). Subsequent dynamic high power tests were conducted at 28 GHz (Halverson et al. "Recent Advances In The Control Of Insects In Stored Products With Microwaves", Paper No. 976098, ASAE Annual International Meeting, Aug. 10–14, 1997) which verified that mortality due to selective heating of insects was superior to that obtained at HF at lower product temperatures, that germination of the wheat was unaffected, and that dynamic treatment of the stored product in a continuous process at high mass flowrates was practicable. Static tests at 28 GHz have verified that the relationship between exposure time and mortality at constant energy input is solely energy dependent for product exposure times greater than 250 milliseconds.

In view of the foregoing physical relationships and test results, the present invention is also directed to systems for controlling insect infestation of a granular product by the transfer of energy from a source or sources of SHF or EHF electromagnetic radiation at high powers to kill the insect while keeping the product temperature at levels where the product quality is unaffected. In one embodiment of the invention, energy from one or more high-power SHF or EHF source is coupled to a continuously flowing granular product in an untuned, metal-walled resonator (an "applicator") through a transmission system. The applicator, through which the infested product to be treated flows freely under the force of gravity, may be cylindrical, rectangular, ellipsoidal, conical, or spherical in form. The input power required is a function of the specified product throughput rate, the energy input per unit mass required to produce the desired level of insect mortality, and the coupling efficiency.

The applicator dimensions are large with respect to a wavelength at the frequency of operation. The applicator couples the electromagnetic energy and the product to achieve a relatively uniform energy density within the product. The applicator also accepts and regulates the flow of a product from an upstream pipe or conduit, and preferably is designed to control the fraction of the total applicator volume occupied by product flowing within the applicator to ensure penetration of the product by the microwave energy.

A process using the applicator is controlled by a system comprising an automatic or manual control station, a permission interlock system to prevent inadvertent operation and flow, temperature, pressure and system status sensors to monitor the process and provide the capability of shutting down the system in the event that the operational safety limits are exceeded. The flow sensors also provide control signals to outside systems which control the mass flow rate of the product.

Both the high-power microwave source and the applicator and the post treatment product will be cooled to remove waste heat through a heat exchanger. The rejected heat provides a means of preheating the product to improve overall operating efficiency.

These and other objects and advantages of the present invention will be apparent in view of the following detailed description.

DETAILED DESCRIPTION OF THE DRAWINGS

Figure 1:
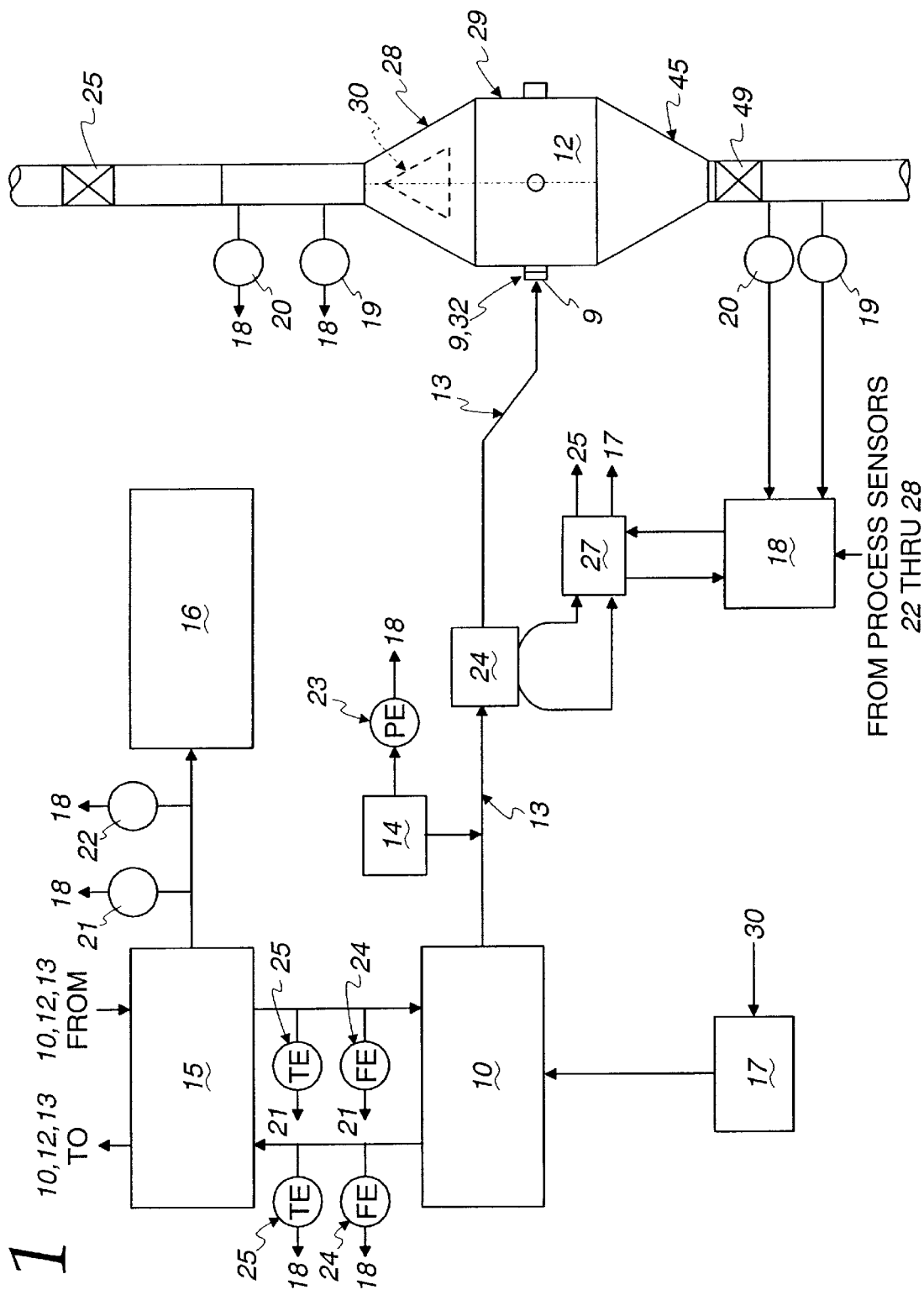
FIG. 1 in a schematic diagram of an apparatus in accordance with the present invention.

One embodiment of the invention is illustrated in FIG. 1 and includes a single source of continuous or pulsed high-power SHF/EHF electromagnetic radiation 10 coupled to an applicator 12 through a waveguide transmission system 13. Additional energy sources may also be coupled to the applicator 12 through parallel identical systems each of which is coupled to the applicator 12 through one of several coupling ports 9 spaced equally about the periphery of the applicator 12. To prevent microwave breakdown in the transmission system 13 at the high input power levels necessary to treat the product continuously at a high-throughput rate, the transmission system 13 will be pressurized by clean dry air, nitrogen, or dielectric gas system 14. A cooling system 15 will provide cooling for the energy source 10, the applicator 12, and the waveguide transmission system 13 and will discharge the waste heat to a regenerative heat exchanger 16 for use in conditioning the grain temperature, either before or after exposure to the electromagnetic radiation in the applicator 12, to increase overall efficiency of the process and increase insect mortality.

A power supply 17 for the microwave source 10 is controlled by the logic in the fully redundant facility safety system 18. The facility safety system 18 monitors the output of upstream and downstream flow sensors 19 and temperature sensors 20 in piping leading to and from the applicator 12, flow sensors 21 and temperature sensors 22 in the cooling system, pressure sensors 23 in both the applicator 12 and the transmission system 13, and a dual directional coupler 24 for monitoring incidental and reflected power.

When predetermined facility safety system setpoints are exceeded, automatic shut down of the system occurs by cutting power to the microwave source 10, closing upstream and downstream shutoff gate valves 25 and cutting power to any powered component in the grain handling system which provides the static pressure head to the flowing grain. A master control station 27 provides a means of energizing the system either manually or automatically when permissive interlocks from the control logic 18 are satisfied.

Figure 2:
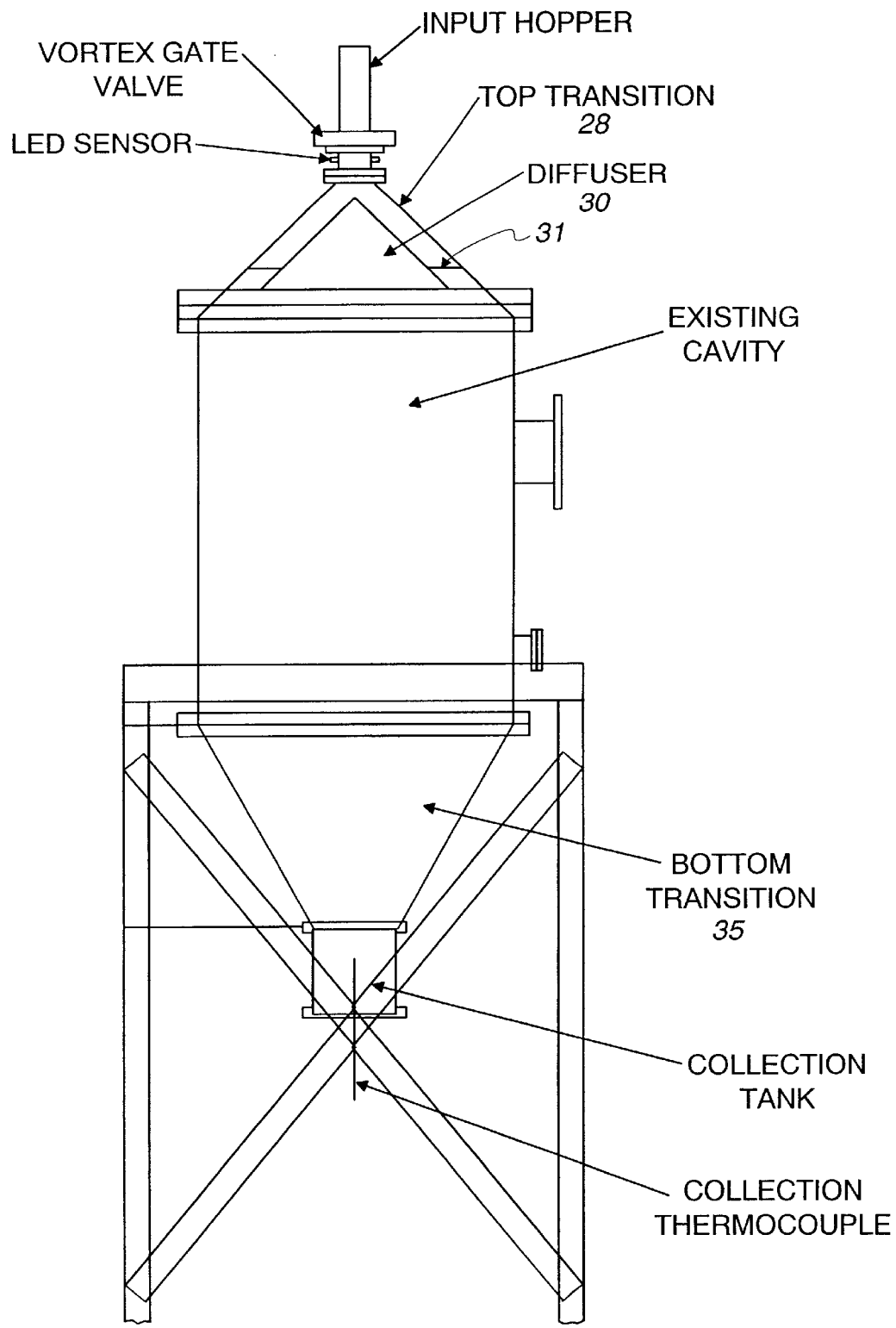
FIG. 2 is an elevational view of an apparatus in accordance with the present invention.
Figure 3A:
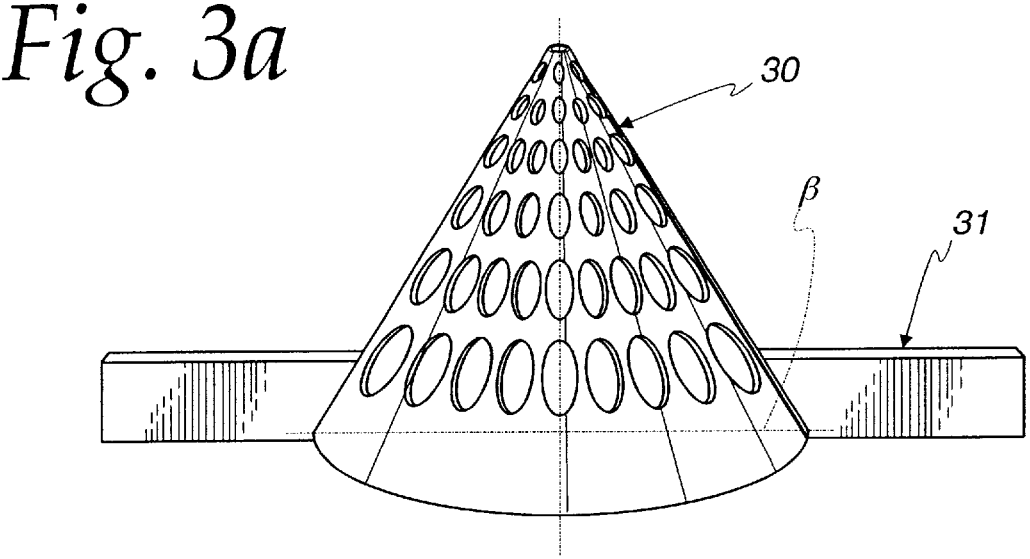
FIG. 3a is a side view of an applicator in accordance with the present invention.

An applicator 12 for the treatment of a dynamic product such as whole, cut or rolled cereal grain, is shown in FIG. 2 in the preferred cylindrical form. It comprises an entry section 28 which is a gradual transition from the dimensions of the inlet piping or conduit to the dimensions of the main applicator chamber 29. The bulk density in the main chamber is controlled by a diffuser 30 and supporting structure 31. The entry section 28, the main applicator chamber 29, the diffuser 30, and the supporting structure 31 are preferably made of, or are lined or plated with, a highly conductive metal such as copper or aluminum to minimize electrical losses during operation. The preferred diffuser 30 is a conical plate with holes to permit the relatively uniform distribution of product downstream. The location and diameter of the holes in the plate is determined mathematically and verified by testing to produce a radially uniform distribution. A preferred diffuser 30 that controls the product-to-air volume ratio for a 3 dB penetration depth at the chosen frequency of operation, is shown in FIG. 3a. The diffuser 30 is a continuous cylindrical cone sieve whose angle is greater than the angle of repose β to overcome any static friction head and consequent flow blockage where:

$$\arctan \beta \geq 0.3$$

The minimum apertures in the diffuser 30 are large enough to prevent blockage of the treated granular material. The cross-sectional area of the apertures through which the product falls increase along the radial surface of the cone so that the probability of a single grain falling through the diffuser 30 is nearly constant over the linear length of the surface of the conical diffuser 30 to ensure that the emerging stream is uniformly distributed in the applicator 12 as it continues to fall under the force of gravity.

Figure 3B:
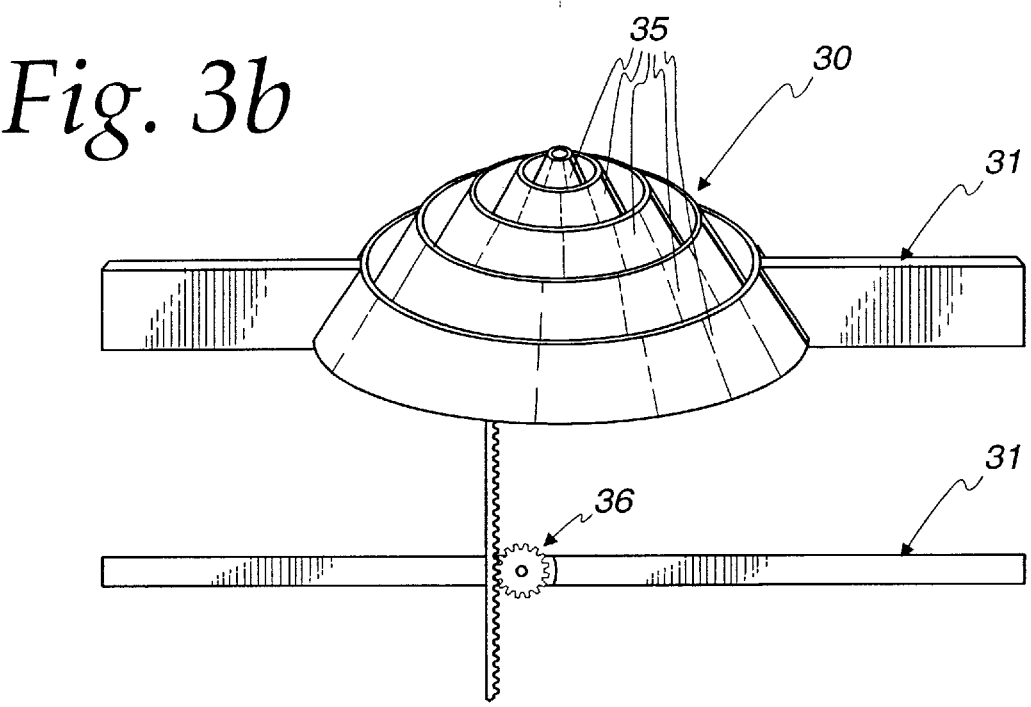
FIG. 3b is a side view of another embodiment of an applicator in accordance with the present invention.

A second embodiment of a diffuser 30 is shown in FIG. 3b. In this case the diffuser 30 includes a number of stacked open-ended truncated cones 35 whose total axial length (vertical height), and hence aperture of the opening between each truncated section 35, can be continuously adjustable by means of a rack and pinion system 36 to achieve approximately uniform distribution of the emerging stream. The number of truncated cone sections 35 is not critical so long as their combined effect is to achieve uniformity in the flowing stream of granular material.

Figure 3C:
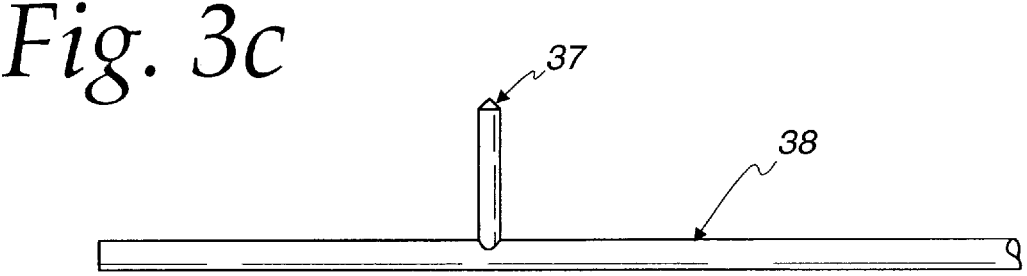
FIG. 3c is a side view of an alternate diffuser embodiment in accordance with the present invention.

A third diffuser embodiment for controlling the product-to-air volume ratio is shown in FIG. 3c, which includes one or more air jet nozzle 37 having sufficient pressure, delivered to the nozzle 37 by pressure piping 38, to disperse the granular product stream as it enters the applicator 12. The diffusers shown in FIGS. 3a and 3b may be either augmented by or replaced completely by the air jet nozzle 37 to meet the uniformity requirements.

The expansion of the flowing stream of bulk product by the diffuser 30 ensures that the grain-to-air volumetric ratio and the consequent bulk density in the applicator 12 is low enough to permit penetration into the flowing grain by the electromagnetic energy within the applicator 12 while keeping the product mass flow rate constant. The electromagnetic energy is coupled to the flowing grain in the applicator 12 by a coupler 32 through any one or more regularly spaced ports 9 in the walls of the applicator chamber 29. Each port 9 is provided with a choke 34 at the inner surface of the applicator chamber 29 to suppress induced currents within the near field of the port 9 and ensure that the energy losses in the walls of the applicator chamber 29 are minimized.

The coupler 32 for each source comprises a waveguide (not illustrated) with an input connector or waveguide flange. Coupling a multiplicity of parallel sources to the applicator 12 is provided by similar input connectors spaced equally around the circumference of the applicator chamber 29. With a plurality of couplers 32, the energy density within the applicator 12 of a length L will be increased n-fold, where n is the number of independent parallel sources. The use of additional couplers 32 will decrease the exposure time required to administer a lethal energy dose to the insects.

The terminal section 45 at the output of the applicator 12 is a transition section to collect the granular product and restore it to the standard flow density. The terminal section 45 is also made of, or is lined or plated with, a highly conductive metal such as copper or aluminum to minimize electrical losses during operation. As the grain is collected it creates a dense, but flowing mass that ensures that any energy which is not dissipated in the grain in the chamber 29 will be dissipated in the product both at the entry section and terminal section thereby reducing or preventing leakage of microwave energy outside the bounds of the applicator 12. A shutoff valve 49 is also included in the downstream piping for purposes of isolating the applicator 12 when safe operating limits are exceeded.

Figure 4:
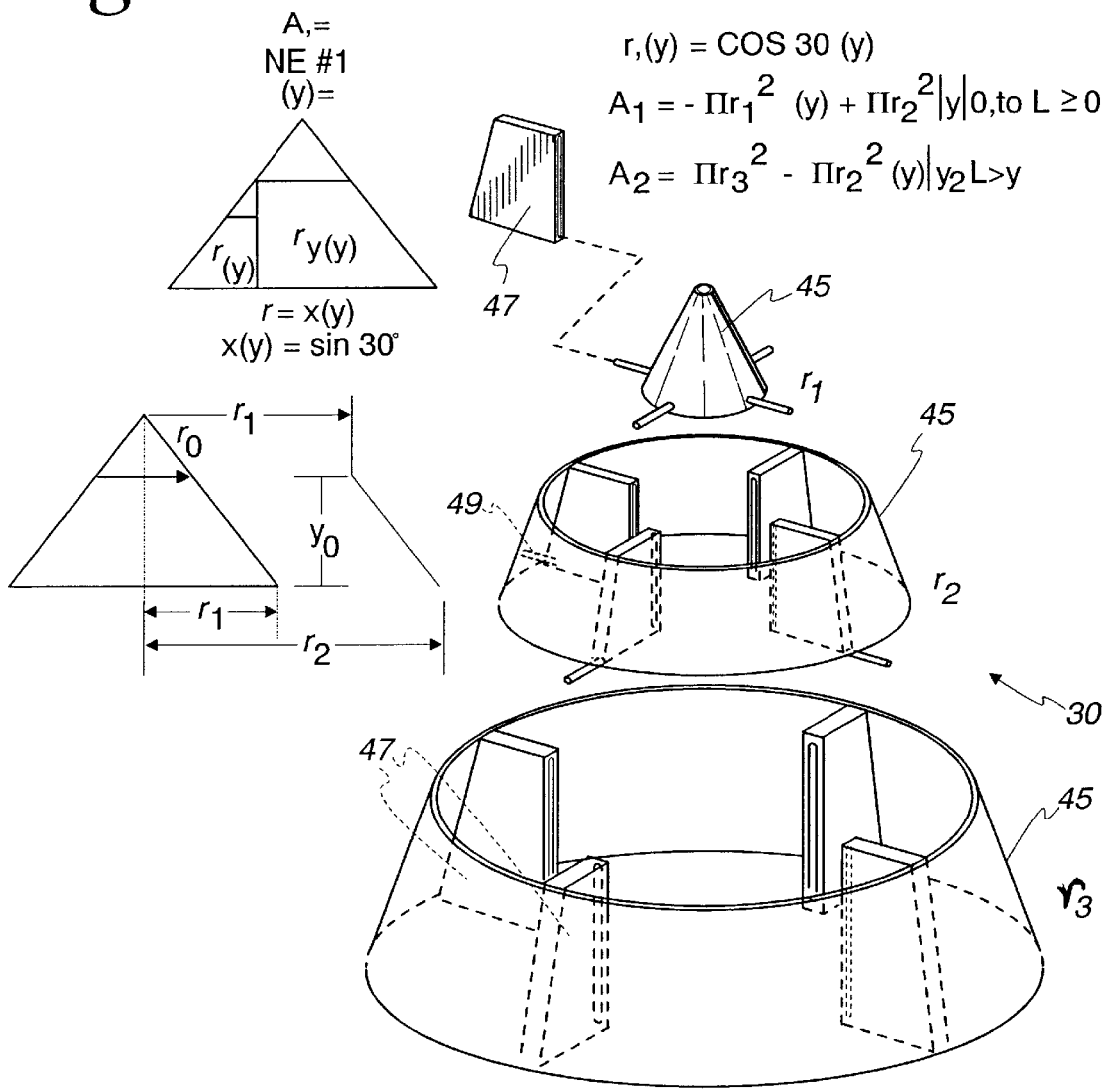
FIG. 4 is an exploded view of an alternate diffuser in accordance with the present invention.

FIG. 4 depicts a diffuser 30 including a plurality of truncated conical-shaped sections 45 maintained in a spaced relationship by slotted spacers 47 and pegs 49 (all preferably made of Teflon). The slots provide for vertical movement of the truncated conical-shaped sections 45 while confining the sections from lateral movement. The pegs 49 maintain a minimum annular gap. The rack and pinion 36 (FIG. 3b) can be connected to the uppermost truncated cone section and when rack and pinion raise the pegs in the top section to the top of the slots in the next-lower section, then the pegs in the next lower section will begin to slide up in the slots of the next section below, and so on until the desired diffuser shape is obtained.

Figure 5:
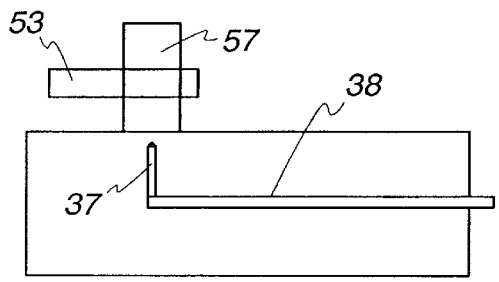
FIG. 5 is an alternate variable air pressure diffuser in accordance with the present invention.

FIG. 5 depicts a pressure pipe 38 having variable flow of pressurized fluid (preferably air) that is emitted from nozzle 37 through a pipe 51 that can be closed using a gate valve 53. The nozzle 37 is centered in the pipe 51. The nozzle 37 is disposed in a cavity 55 with a grain collection cone in the bottom.

Excitation of an infested product at frequencies within the free water relaxation band above 18 GHz to enhance selective heating of insects has been tested at a frequency of 28 GHz with load energies ranging from 20 to 62 J per gram of infested product. Both dynamic (flowing) and static samples of soft white wheat Triticum aestivum (L.) infested with adults and larvae of the maize weevil, Sitophilus zeamais Motschulsky were exposed in a detuned resonant cavity ("applicator"). A mortality of approximately 100% for adults and older larvae (and pupae) and greater than 94% for the younger larvae (and eggs) was achieved in both cases. However, the efficiency of energy coupling in the dynamic case was nearly twice as great as the static. Maximum product temperatures ranged from 35 to 52 degrees C. Subsequent measurements of penetration depth of a singly traveling plane wave in a flowing grain-air mixture, including wheat and rice, indicated penetration depths of 30 to 38 cm.

Recent tests have concluded that selective heating of the insect increases nonlinearly at frequencies above 10.6 GHz and that relaxation processes associated with free water in the insect and increased energy transfer to electrically small bodies at frequencies greater than 24 GHz would produce enhanced selective heating since the stored cereal grains contain water only in the bound form. Both dynamic (continuous process) and static (batch process) tests were conducted at 28 GHz at the Oak Ridge National Laboratory (ORNL) Fusion Engineering DivisionÆs 200 kW VGA-8000 (CPI, Palo Alto, Calif.) CW gyrotron facility on samples of soft white wheat, Triticum aestivum (L.), infested with adults and larvae of the maize weevil, Sitophilus zeamais Motschulsky. The results of this test, reported in Halverson et al. 1997 (incorporated herein by reference), demonstrated the practicability of continuous processing of stored products at high mass flowrates.

The dynamic tests verified that control of the air-to-product volume ratio in a detuned resonant cavity ("applicator") would result in deeper penetration of energy into a diffused dynamic (flowing) product and to determine the relationship between energy, product temperature, and insect mortality in the flowing product. (This test is discussed from the entomological standpoint in a paper in this conference by R. Plarre et al., Microwaves at higher frequencies-can they be use for stored product pest control). A prototype applicator to treat the infested dynamic product was designed and constructed for treatment at a frequency of 28 GHz. The applicator was cylindrical (1 m long×0.78 m diameter) and included a means of controlling the volume ratio of the product. Inside of the applicator was a 10.16 cm diameter quartz tube to control the depth of penetration of the flowing bulk product. Exposure time in the prototype applicator was determined by the length of time for a single grain to fall under the force of gravity through the 1 m long applicator. Test samples were released from a test hopper and flowed through the applicator where they were exposed to the microwave energy for the fixed 600 ms time-of-transit period and then collected in a sample holder at the output. The results indicated 100% kill of adults, pupae and old larvae, and greater than 94% of the young larvae and eggs over a minimum energy range per unit mass of product of about 20 to 75 J/g at maximum product temperatures of 36 degrees C., about 44 degrees C. and about 52 degrees C. as shown in Tables 2(a) and 2(b).

A comparison of the dynamic 28 GHz adult mortality at 7*d* versus temperature data with that of static tests at 39 MHz at 8*d* (Nelson and Stetson 1974) for adult rice weevils indicates that mortality at 28 GHz as a function of maximum grain temperature for the adult maize weevils appears to be identical within the statistical variance of the data. Since the load energy was not reduced to the level where 50% mortality occurred, the dynamic test alone could not demonstrate the expected increase in the selective heating of the insect compared to the 39 MHz case. However, enhanced selective heating was demonstrated in the static test. No comparisons of mortality as a function of load energy could be made because comparable published data at 39 MHz were not available.

In the case of the static tests at 28 GHz where exposure time was variable, a −3 dB thick layer (7 mm) of product containing capsules of infested soft white wheat was exposed for various periods of time from 250 ms to two seconds to determine the relationship between mortality and exposure time at various inputenergies. The results shown in Table 1 confirmed that energy was the dominant factor in determining mortality for exposure times as short as 500 ms. The temperatures given were taken by a single type K thermocouple located at the center of the 39.4 cm diameter dish which held the exposed static mass. Post exposure infrared scan recordings of the dish indicated that the spatial temperature distribution in the dish was lower than that at the thermocouple and therefore the measured temperature range given in Table 1 represents an upper bound to both the maximum and minimum values given. Hence, the knee of the logistic mortality curve for the 7*d* adult mortality was actually lower than temperatures reported by others at 39 MHz and supports the thesis that coupling to the free water in the insect is a more efficient way of transferring energy than by coupling to bound water.

In both dynamic and static tests at 28 GHz the adults and older larvae were killed more easily at lower input energies and lower product temperatures than the younger larvae. This implied that, in the case of adults and older larvae, the dominant energy transfer mechanism to the insect is by direct radiation rather than indirectly by conduction from the heated product. In the case of the younger larvae and eggs, radiation coupling may be diminished because of its much smaller energy cross section and the shielding effects of the wheat kernel in which they reside. Nevertheless exposure times of 600 ms were sufficiently long to kill the larvae but required greater energy input to do so with resulting higher product temperatures. Older larvae are also somewhat shielded by the kernel but less than the younger because the older larvae have already excavated most of the inner matter in the kernel and, thus are only shielded by a very thin layer.

One-way path attenuation tests were conducted on dynamic (flowing) samples of hard red wheat, soft white wheat, and long grain brown rice over a range of 18 to 50 GHz to validate previous calculations of increased penetration for the dynamic state (Halverson et al. Engineering Design of High-Power Microwave Applicators for Stored Product Protection, Paper 986052, ASAE Annual Meeting, 1998, incorporated herein by reference). This provided a direct measure of the depth of penetration of a singly traveling wave through the flowing product over a path length of 10.16 cm. This path length was chosen because it was identical to the diameter of the quartz tube used in the dynamic test. Three replicates of cultivars of hard red wheat, soft white wheat and brown rice were tested in the dynamic (flowing) state over each of three swept frequency ranges, 18 to 26.5 GHz, 26.5 to 40 GHz and 33 to 50 GHz and the one-way path attenuation between transmitting and receiving horns was measured directly. Prior to the direct measurement, penetration depth had been inferred from measurements of the dielectric properties of the bulk product by using the Landau, Lifschitz and Looyenga (Nelson and You 1990) equations for dielectric mixtures. The depth of penetration was then calculated from the attenuation constant for a specified air-product mixture. The direct measurements of soft white wheat were in agreement with the calculated values and demonstrated the random complex scattering properties of the flowing mass. Initial results indicate average penetration depths of about 30 cm were achieved at 28 GHz for volume ratios about 3%. It was also noted that both scattering and absorption occur within the flowing product. The former tends to act as a mode stirrer thus leading to greater field uniformity within the applicator. The microwave energy within the detuned cavity applicator may be thought of as a photon gas.

Ancillary static tests were performed at the University of Wisconsin at Madison on the Computer and Electrical Engineering Department ÆS 14.25 GHz facility (Plarre et al. 1997) to verify the relationship between exposure time and mortality at a constant energy input. This test also involved exposure of samples of soft white wheat infested with maize weevils. The exposed samples were observed for mortality over a $35d$ period. The results indicated that for the case of treatment of a static product exposure time has a lower limit in producing a high mortality with low variability. A comparison with data taken in the static test at 28 GHz shown in Table 1 indicates that the minimum exposure time appears to be facility and frequency specific. In particular the microwave power coupling efficiency (k) was much lower in the 14.25 GHz facility than in the 28 GHz facility. Therefore, to permit a normalized comparison of the results the exposure time per unit mass of product the variable k(t/m is introduced as defined in Table 1. The results indicate that for the constant energy case mortality appears to be a nonlinear function of exposure time once the lower exposure time limit has been reached. This limit was unique for each of the two test facilities and protocols studied here.

TABLE 2(a)

Mortality of maize weevils in soft white wheat in the dynamic test at 28 GHz versus maximum product temperature $T_{max}$.

(a)

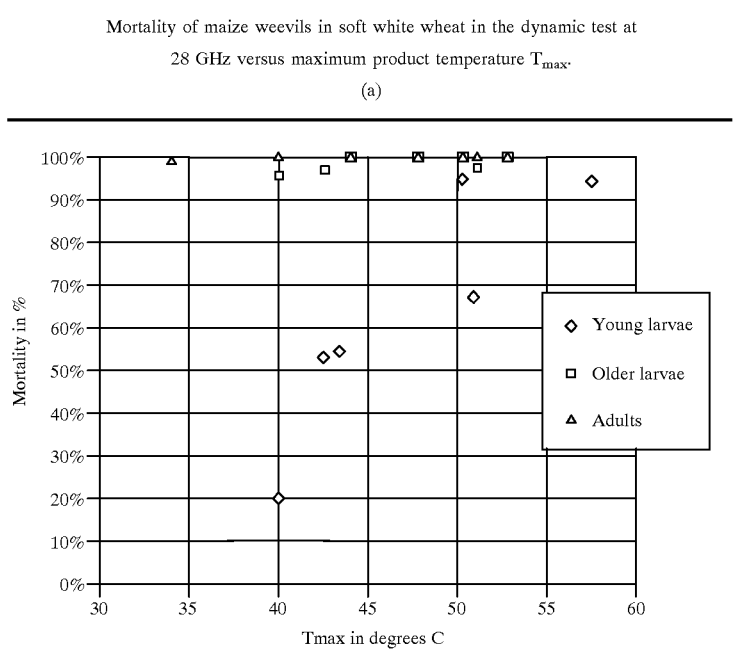

TABLE 2(b)

Mortality of maize weevils in soft white wheat in the dynamic test at 28 GHz versus $U_{load}$.

(b)

*[Chart: Mortality in % vs Uload in J/g, showing data points for Young larvae (◇), Older larvae (□), and Adults (△), with Uload ranging from 30 to 60 J/g and mortality ranging from 0% to 100%]*

The depth of penetration calculations based on the complex dielectric properties of the medium were validated by the results of the depth of penetration measurements previously described. Therefore, the following theoretical equations may now be used to establish the design requirements for an applicator where the product is uniformly distributed by a diffusion means.

The depth of penetration of electromagnetic fields into the bulk material in the applicator is normally characterized by the inverse of the attenuation constant or penetration depth of the bulk material. The penetration depth is that distance over which the intensity of a singly traveling plane wave will be reduced by a factor of 1/e of its initial value. A derived characteristic, the depth of penetration (Metaxas and Meredith 1993), defined by a −3 dB attenuation depth, or that depth over which the intensity of a singly traveling plane wave will be reduced by a factor of may also be used. The attenuation is related inversely to the density-dependent effective loss factor of the bulk material and the frequency. As frequency increases the penetration depth in a dense and lossy material decreases rapidly. Therefore, in a mass flowing freely under the gravitational force, it is necessary to provide a means of controlling the bulk density to permit the energy to penetrate the product. The −3 dB penetration depth, defined by equation (1) is dependent upon the complex dielectric properties of the individuals comprising the heterogeneous mixture of insects and product in the applicator. The attenuation of the wave intensity per unit length for a plane wave propagating through the mixture can be determined from the equation (2), derived from the propagation constant in complex dielectrics (Ramo and Whinnery 1953) and the dielectric mixture equation (3).

$$\delta_{3dB} = 0.3466/\alpha \quad (1)$$

Where:

$$\alpha = \omega \sqrt{\mu_o \epsilon O \epsilon_r} \cos(\tfrac{1}{2} \arctan(-\epsilon_r''/\epsilon_r' \pm 2\pi) + \pi/2) \text{ Nepers per meter} \quad (2)$$

$\mu_o = 4\pi(10)^{-7}$ Wb/m $\epsilon_o = \tfrac{1}{36}\pi(10)^{-9}$ F/m $\epsilon_r$=Relative complex dielectric constant of mixture.

$= \epsilon'_r - j\epsilon''_r$ $\epsilon''$=Loss Factor $\epsilon'_r$=Real part of relative dielectric constant $\omega = 2\pi f$ Hz.

From Nelson and You, 1990:

$$\epsilon_r^{1/3} = v2(\epsilon_r \text{ LLL})^{1/3} + v1(\epsilon_r \text{ air})^{1/3} \quad (3)$$

$\epsilon_r$ LLL is the relative complex dielectric constant of the individual infested kernel determined from independent measurements of $\epsilon_r$ for the infested product $\epsilon_r LLL = \epsilon_r' LLL + j\epsilon_r'' LLL$ $\epsilon_r$ air=1

$v1$=Ratio of the volume of air in the mixture to the total applicator volume=$1 - v_2$ $v2$=Ratio of the volume of infested kernels in the mixture to the total applicator volume.

General solutions for the half-power (−3 dB) depth of penetration of the fields into the granular medium may as a function of $v_2$ can be determined by letting $v_2$ be an independent variable and solving for $v_1$ and substituting values in equations (2), (3) and (1).

To determine $v_2$ in a particular case, where the system design requirements are established, the following design specifications must be known. The mass flowrate $f_m$ of the orifice gate valve of a specified inlet orifice of radius $r_o$. The average weight $m_k$ and average volume $V_k$ of a single kernel of treated grain determined by measurement or from published data.

The axial length L and volume V of the cylindrical applicator. The average velocity $v_k$ of a single kernel of grain falling under the force of gravity through the axial length of the applicator.

Given $v_k$ and L the dwell time of a single kernel in the applicator will be:

$$t_d = L/v_k \quad (4)$$

Therefore, the total mass of the uniformly distributed product within the applicator at any time will be:

$$\Sigma m_k = f_m * t_d \quad (5)$$

the total number of kernels in the applicator will be:

$$N_k = \Sigma m_k / m_k \quad (6)$$

and the total volume occupied by the total mass of product in the applicator will be:

$$\Sigma V_k = N_k * V_k \quad (7)$$

Hence, the volume of product normalized with respect to V is:

$$v_2 = \Sigma V_k / V \quad (8)$$

and the normalized volume of air is:

$$v_1 = 1 - v_2 \quad (9)$$

Substituting the above values in (3) will yield particular solutions to (2) and (1). The particular solution is then compared to the general solution to determine if the penetration depth criterion, i.e. that the distance from any coupling aperture to the product within the applicator is equal or less than the −3 dB penetration depth defined by equation (1). If the penetration depth criterion is not met then the design specifications of the system must be changed by either decreasing the mass flowrate $f_m$ or increasing the applicator volume V until the criterion is met. The input power requirements to produce the desired level of mortality may now be determined from the following equation in cases where the 100% lethal specific load energy ($U_{load100}$) and coupling efficiency (k) have been determined from test data.

$$P_{in} = (U_{load100}/(k * t_d)) * \Sigma m_k$$

The coupling between the gyrotron oscillator and the treated product in a dynamic state is greater than for the static mass as determined by the calculated coupling coefficient (Halverson et al. 1997). This implies greater system efficiency in dynamic treatment and consequently indicates the practicability and advantages of continuous processing of a diffused infested product. By taking the advantage of the extremely high continuous power generation capability of the gyrotron, the process throughput rate can be increased substantially thereby eliminating the limitations of batch processing at lower powers. The design of the dynamic prototype facility is being modified presently to permit processing at an equivalent rate of 4½ to 9 kg/s. Successful completion of a dynamic test on the modified facility is a necessary precursor to the development of a demonstration unit capable of processing at a rate required by a typical storage facility by the year 2000.

Table 1. Linear mortality curve fitting for the variables of load energy per unit product, maximum temperature, and exposure time/mass, for the static test at 28 GHz.

| Age | $M(U_{load})\%$ $22 \leq U_{load} \leq 44$ J/g | $M(T_{max})\%$ $35 \leq T_{max} \pm 46°$ C. | $M(t)\%$ ($U_{in}$ = constant) $0.42 \leq k\Delta t/m \leq 6.6$ ms/g |
|---|---|---|---|
| Young larvae | $0.28\ U_{load} + 84.4$ | $0.57\ T_{max} + 70.23$ | $2.23\ k\Delta t/m + 84.4$ |
| Older larvae | 100 | 100 | 100 |
| Adults | 100 | 100 | 100 | where:

$U_{in} = U_{in}/m$ [J/g] is the specific energy input in terms of $U_{in}$ per unit mass of product $U_{load} = kU'_{in}$ $= C\Delta T$ [J/g] is the amount of energy delivered to the sample per unit mass $k = Cm\Delta T/U_{in}$ is the coupling coefficient $U_{in} = P\Delta t$ [W −s] or [J]

m is the measured sample mass in grams [g]

$\Delta t$ is the measured exposure time in seconds [s]

Tmax is the measured maximum sample temperature in ° C.

P is the measured input power in watts [W]

C is the specific heat of soft white wheat [J/g−° C.]

The forgoing detailed description of the invention is provided for clearness of understanding only and no unnecessary limitations therefrom should be read into the following claims.

What is claimed is:

1. A granular material applicator for mixing granular material with air prior to microwave insecticide treatment of the granular material in a main applicator chamber, the applicator comprising:

an entry section having an inlet of a first cross-sectional area and an outlet of a second cross-sectional area that is larger than the first cross-sectional area; and a grain diffuser disposed in the entry section between the inlet and the outlet, and the grain distributor defines a plurality of grain flow orifices.

2. The granular material applicator of claim 1, wherein the entry section is conical in shape.

3. The granular material applicator of claim 1, wherein the entry section is conical in shape, and the inlet and outlet define circular cross-sectional areas.

4. The granular material applicator of claim 1, wherein the grain diffuser is conical in shape.

5. The granular material applicator of claim 1, wherein the grain diffuser includes a plurality of inverted truncated cones of increasing diameter and defining annular grain flow orifices therebetween.

6. The granular material applicator of claim 1, wherein the grain diffuser is adjustable between the inlet and outlet.

7. The granular material applicator of claim 1, wherein the grain diffuser includes a plurality of inverted truncated cones of increasing diameter and defining annular grain flow orifices, and the inverted truncated cones are maintained in a spaced relationship by spaces radially spaced around the annular grain flow orifices.

* * * * *